United States Patent
Chen

(10) Patent No.: US 8,988,231 B2
(45) Date of Patent: Mar. 24, 2015

(54) WETNESS NOTIFICATION SYSTEM

(71) Applicant: Hung Chi Chen, Kaohsiung (TW)

(72) Inventor: Hung Chi Chen, Kaohsiung (TW)

(73) Assignee: I-Ding Medical Equipment Co., Ltd., Kaohsiung (TW)

( * ) Notice: Subject to any disclaimer, the term of this patent is extended or adjusted under 35 U.S.C. 154(b) by 96 days.

(21) Appl. No.: 13/973,871

(22) Filed: Aug. 22, 2013

(65) Prior Publication Data
US 2014/0266734 A1 Sep. 18, 2014

(30) Foreign Application Priority Data
Mar. 15, 2013 (TW) ............... 102204794 U

(51) Int. Cl.
G08B 23/00 (2006.01)
G08B 21/20 (2006.01)
A61F 13/42 (2006.01)

(52) U.S. Cl.
CPC ............. *G08B 21/20* (2013.01); *A61F 13/42* (2013.01)
USPC ...................................... 340/573.5

(58) Field of Classification Search
CPC ................................ A61F 13/42; G08B 21/20
USPC ................................ 340/573.5
See application file for complete search history.

(56) References Cited

U.S. PATENT DOCUMENTS

| 4,106,001 | A | 8/1978 | Mahoney |
| 5,036,859 | A | 8/1991 | Brown |
| 5,568,128 | A | 10/1996 | Nair |
| 6,097,297 | A | 8/2000 | Fard |
| 2003/0011479 | A1* | 1/2003 | Bluteau ............ 340/573.5 |
| 2005/0046578 | A1* | 3/2005 | Pires ............... 340/573.5 |

FOREIGN PATENT DOCUMENTS

WO WO 96/25904 A1 8/1996

* cited by examiner

*Primary Examiner* — Steven Lim
*Assistant Examiner* — Omeed Alizada
(74) *Attorney, Agent, or Firm* — Pro-TECHTOR International Services; Ian B. Oglesby

(57) ABSTRACT

A wetness notification system includes a detection unit, a clip unit and a receiver unit. The detection unit includes a sleeve body, a moisture detector, a casing, a processor, a wireless transmitter, and a battery. The processor configures the wireless transmitter to transmit a moisture signal outputted by the moisture detector when the moisture signal corresponds to a moist condition. The clip unit clips the detection unit onto the clothing article. The receiver unit includes a wireless receiver, a controller, and a notification module. When the controller receives the moisture signal via the wireless receiver, the controller drives the notification module to output a wetness notification signal.

11 Claims, 5 Drawing Sheets

WETNESS NOTIFICATION SYSTEM

CROSS-REFERENCE TO RELATED APPLICATION

This application claims priority of R.O.C. application no. 102204794, filed on Mar. 15, 2013.

BACKGROUND OF THE INVENTION

1. Field of the Invention

The present invention relates to a wetness notification system.

2. Description of the Related Art

R.O.C patent no. M403327 discloses a diaper having a wetness sensing device. The diaper includes a first non-woven fabric layer, two strip electrodes, a second non-woven fabric layer, a liquid absorbing layer made from a liquid absorbing material, a liquid-proof layer and two metallic sockets. A first side of the first non-woven fabric layer absorbs a liquid excreted from a human body, and the liquid permeates to a second side of the first non-woven fabric layer. The strip electrodes are attached onto the second side of the first non-woven fabric layer, and the strip electrodes are electrically connected when they come into contact with the liquid. A first side of the second non-woven fabric layer is attached to the second side of the first non-woven fabric layer and to the strip electrodes, and the strip electrodes are thus retained between the first and second non-woven fabric layers. The first side of the second non-woven fabric layer absorbs the liquid, which permeates to a second side of the second non-woven fabric layer. The liquid absorbing layer is attached to the second side of the second non-woven fabric layer, and absorbs that liquid permeated through the second non-woven fabric layer. The liquid-proof layer is made from a liquid proof material. A first side of the liquid-proof layer is attached to the second side of the liquid absorbing layer, and retains the liquid that permeated through the liquid absorbing layer to prevent the liquid from leaking out of the diaper. Each of the metallic sockets has a first engaging portion that engages with a respective one of two engaging bodies of an electrical detection device. This enables the electrical detection device to detect the electrical conduction between the strip electrodes when a liquid is excreted, and to send a wetness notification signal for notifying a guardian to change diaper according to the wetness notification signal.

However, the electrical detection device requires a battery for operation. Due to absence of a low battery notification mechanism for notification when the battery is low in power, untimely changing of the diaper may lead to skin allergy, rashes and other skin diseases. Moreover, the strip electrodes are sewn into the diaper, and sewing increases labor costs and may cause a rise in defective products.

SUMMARY OF THE INVENTION

The object of the present invention is to provide a wetness notification system for detecting wetness in a clothing article that is configured for absorbing urine.

Accordingly, the wetness notification system of the present invention includes a detection unit, a clip unit, and a receiver unit.

The detection unit includes a sleeve body, a moisture detector that is connected to an outer side surface of the sleeve body and that outputs a moisture signal corresponding to a surrounding moisture detected thereby, a casing, a processor that is disposed in the casing and that is electrically connected with the moisture detector, a wireless transmitter that is disposed in the casing and that is electrically connected with the processor, and a battery that is disposed in the casing and that provides electric power to the moisture detector, the processor and the wireless transmitter. The processor receives the moisture signal outputted by the moisture detector, and configures the wireless transmitter to transmit the moisture signal when the moisture signal, corresponds to a moist condition of the surrounding moisture detected by the moisture detector.

The clip unit includes a first portion removably inserted into the sleeve body, a curved second portion that extends from the first portion, and a third portion that extends from the curved second portion. The casing is removably disposed on the third portion of the clip unit. The third portion cooperates with the first portion to clip the detection unit onto the clothing article in a manner that the sleeve body and the moisture detector are disposed at an inner side of the clothing article and that the third portion is disposed at an outer side of the clothing article.

The receiver unit includes a wireless receiver to communicate wirelessly with the wireless transmitter, a controller electrically connected with the wireless receiver, and a notification module electrically connected with the controller. When the controller receives the moisture signal via the wireless receiver, the controller drives the notification module to output a wetness notification signal.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
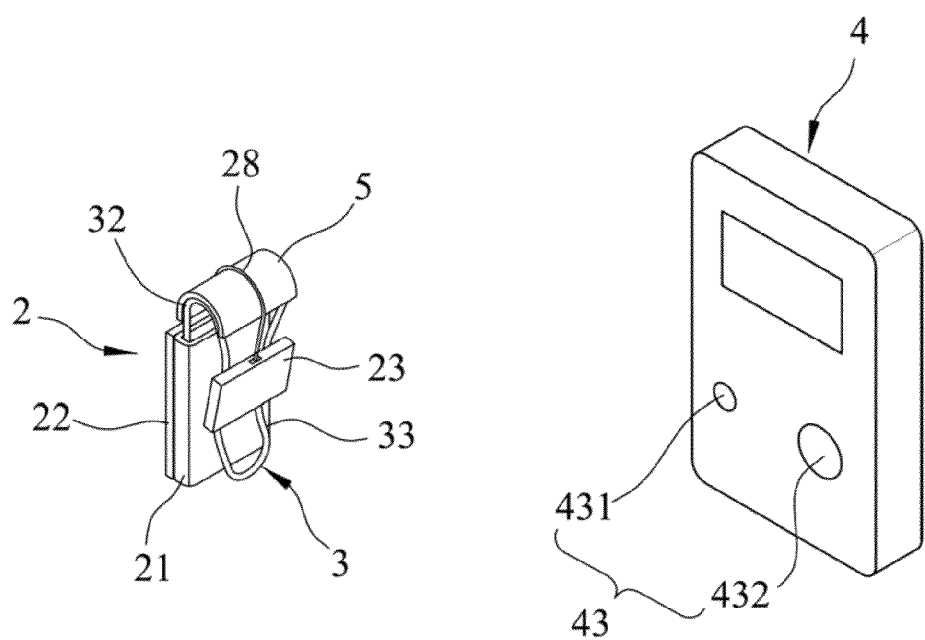
FIG. 1 is a perspective view of a first preferred embodiment of a wetness notification system of the present invention.
Figure 2:
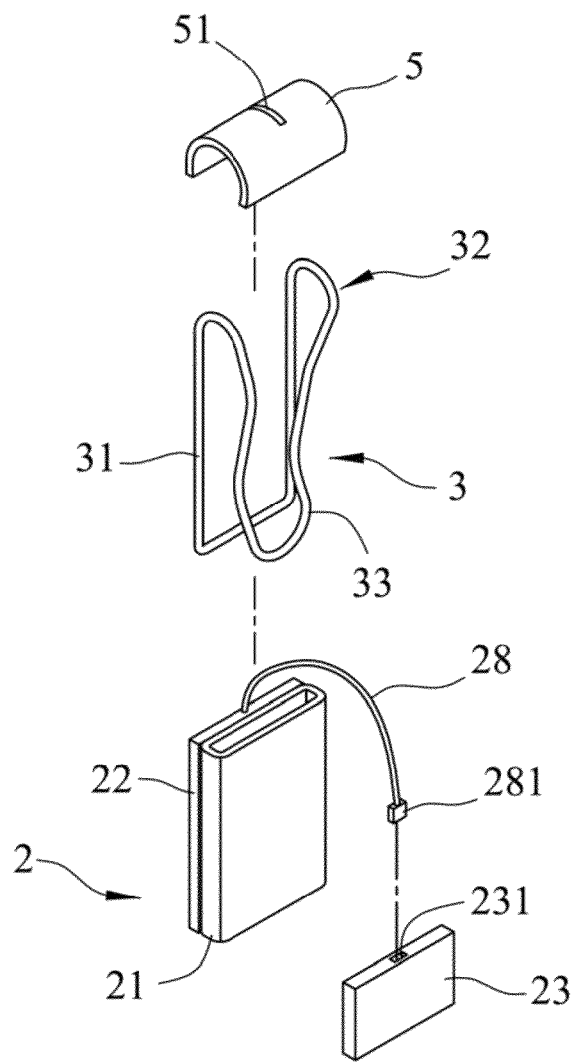
FIG. 2 is an exploded perspective view illustrating a detection unit and a clip unit of the first preferred embodiment.
Figure 3:
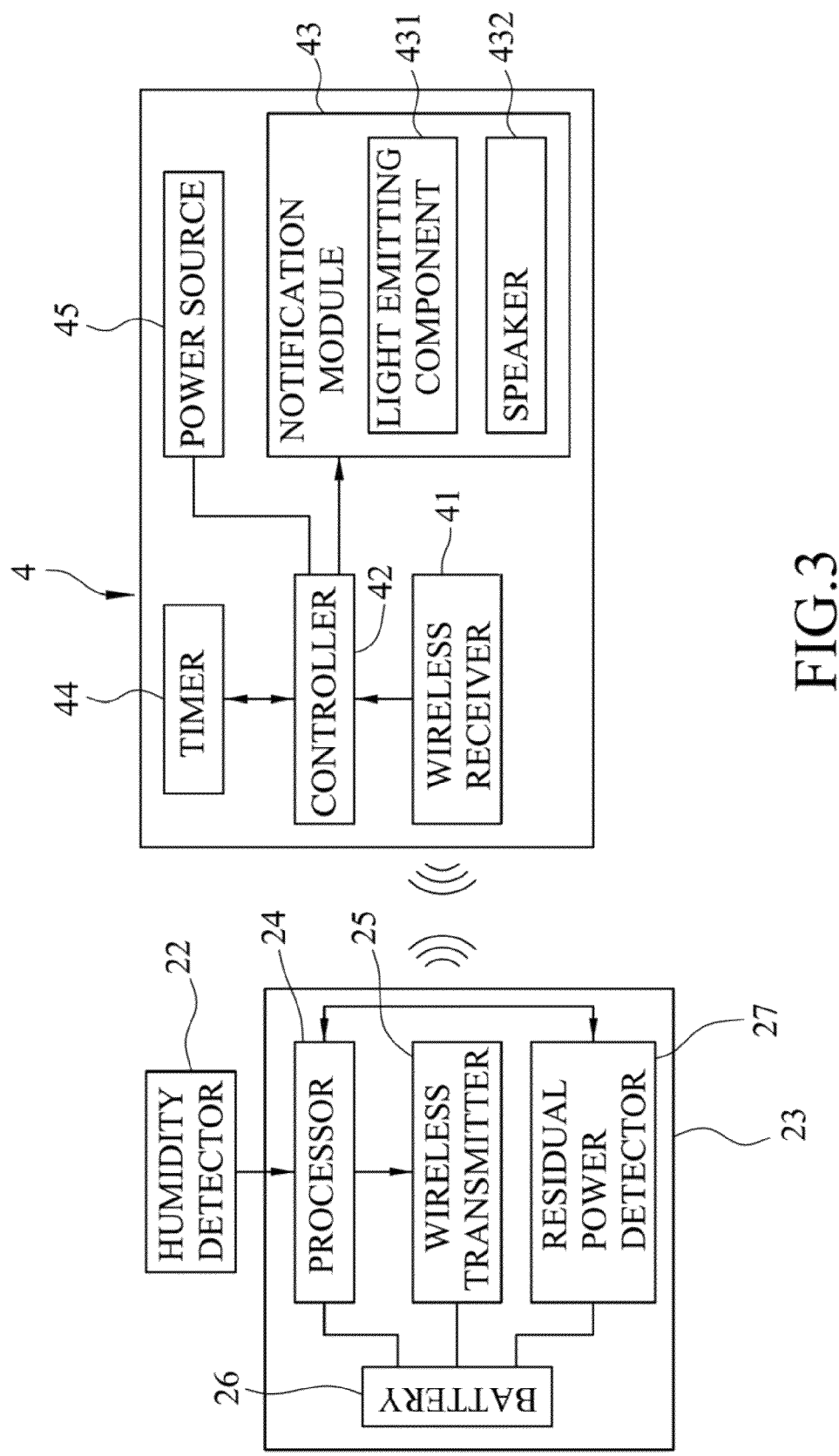
FIG. 3 is a schematic block diagram of the first preferred embodiment.

Referring to FIGS. 1, 2 and 3, the first preferred embodiment of a wetness notification system of the present invention includes a detection unit 2, a clip unit 3 and a receiver unit 4. The detection unit 2 includes a sleeve body 21, a moisture detector 22 that is connected to an outer side surface of the sleeve body 21, a casing 23, a processor 24 that is disposed in the casing 23 and that is electrically connected with the moisture detector 22, a wireless transmitter 25 that is disposed in the casing 23 and that is electrically connected with the processor 24, and a battery 26 that is disposed in the casing 23 and that provides electric power to the moisture detector 22, the processor 24 and the wireless transmitter 25. The detection unit 2 further includes a residual power detector 27 that is disposed in the casing 23 and that is electrically connected with the battery 26 and the processor 24, and a transmission wire 28. The casing 23 includes a connector 231. The battery 26 is electrically connected with the moisture detector 22, the wireless transmitter 25 and the residual power detector 27. One end of the transmission wire 28 connects electrically with the moisture detector 22, and the other end of the transmission wire 28 includes a plug 281 that plugs into the connector 231 of the casing 23 to electrically connect the moisture detector 22 with the processor 24.

The clip unit 3 is a hollow frame made from a bent resilient loop-shaped member, and has a first portion 31 removably inserted into the sleeve body 21, a curved second portion 32 that extends from the first portion 31, and a third portion 33 that extends from the curved second portion 32. that the third portion 33 has the casing 23 removably disposed thereon, and cooperates with the first portion 31 to clip the detection unit 2 onto the clothing article. The width of the third portion 33 is smaller than the width of the first portion 31.

The receiver unit 4 includes a wireless receiver 41 to communicate wirelessly with the wireless transmitter 25, a controller 42 electrically connected with the wireless receiver 41, a notification module 43 electrically connected with the controller 42, a timer 44 electrically coupled with the controller 42 and storing a predetermined period value, and a power source 45 electrically coupled with the controller 42 to provide electric power to the receiver unit 4. The controller 42 has a normal notification mode and a looping notification mode, which will be described in greater detail in the following paragraphs. The notification module 43 includes a light emitting component 431 for emitting light and a speaker 432 for outputting sound. The timer 44 can be integrated into the controller 42 such that the controller 42 is capable of counting in other embodiments of this invention. The frequency used between the wireless transmitter 25 and the wireless receiver 41 can be preset in the factory. The frequency can also be calibrated by the user using a tuner (not shown in the Figures) in other embodiments of this invention.

Preferably, the wetness notification system further includes a positioning member 5 that is provided on the clip unit 3 and that positions the transmission wire 28 on the clip unit 3. The positioning member 5 includes a slit 51 for receiving a section of the transmission wire 28.

Figure 4:
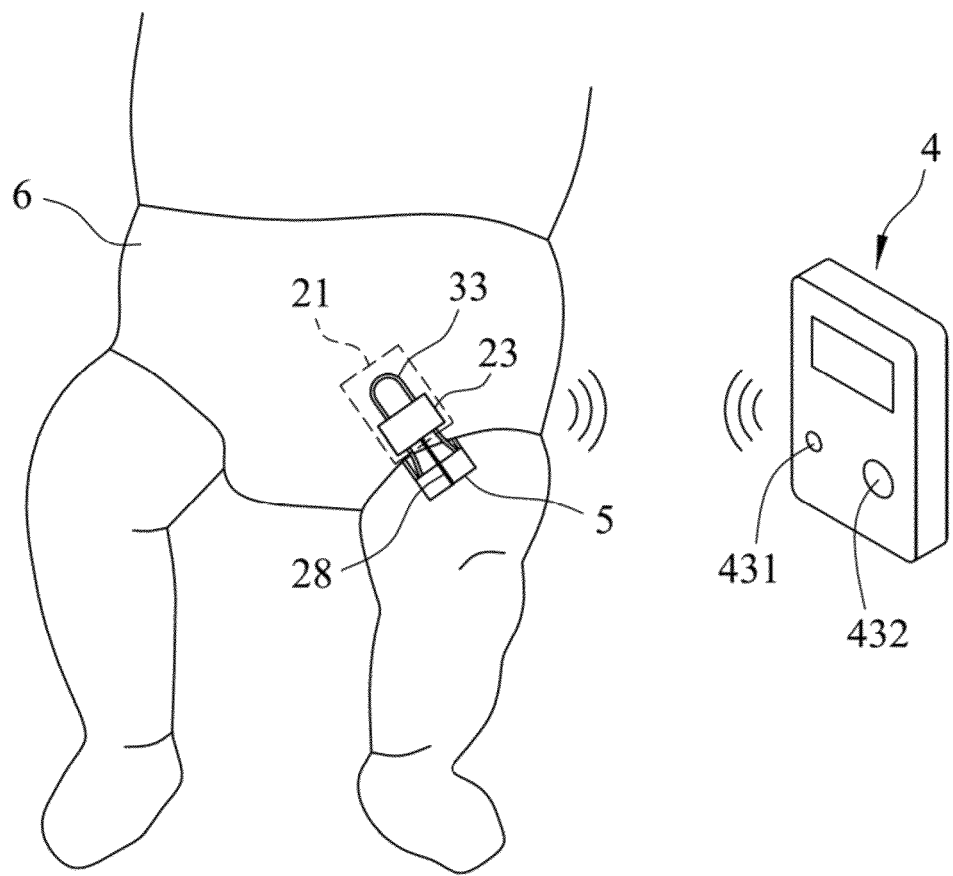
FIG. 4 is a schematic view illustrating the first preferred embodiment when in a state of use.

Referring to FIGS. 1, 2 and 4, the wetness notification system can be applied on a clothing article such as a diaper or a pant, wearable by a person. In use, the first portion 31 is removably inserted into the sleeve body 21, the casing 23 is removably disposed on the third portion 33 of the clip unit 3, the transmission wire 28 is positioned by the slit 51 of the positioning member 5, and the plug 281 is plugged into the connector 231 of the casing 23. The sleeve body 21 and the moisture detector 22 are disposed at an inner side of the clothing article 6, preferably adjacent to the groin of the human body, and the third portion 33 is disposed at an outer side of the clothing article 6. The clip unit 3 is a hollow frame that has a light weight which reduces the load on the user. The curved second portion 32 has a curved design that can enhance user comfort in spite of the detection unit 2. The receiver unit 4 can be carried around by a guardian or be placed at a specific location that can be seen by the guardian.

Referring to FIG. 3, the moisture detector 22 outputs a moisture signal corresponding to a surrounding moisture detected thereby, that is, the moisture around the groin area when the detection unit 2 is clipped onto the clothing article 6. The processor 24 receives the moisture signal outputted by the moisture detector 22, and configures the wireless transmitter 25 to transmit the moisture signal when the moisture signal corresponds to a moist condition of the surrounding moisture detected by the moisture detector 22, that is, when urine is excreted by the user of the clothing article 6. The controller 42 receives the moisture signal through the wireless receiver 41 of the receiver unit 4. When the controller 42 receives the moisture signal for a first time via the wireless receiver 41, the controller 42 executes the normal notification mode to configure the notification module 43 to output a wetness notification signal, and at the same time configures the timer 44 to start counting. The controller 42 configures the notification module 43 to stop outputting the wetness notification signal when the timer 44 has counted to the predetermined period value. The wetness notification signal is at least one of the light emitted by the light emitting component 431 and the sound outputted by the speaker 432, thereby alerting the guardian to attend to changing of the clothing article 6.

After the notification module 43 stops outputting the wetness notification signal when the timer 44 has counted to the predetermined period value, if the controller 42 continues to receive the moisture signal via the wireless receiver 41, the controller 42 executes the looping notification mode to configure the notification module 43 to output the wetness notification signal intermittently until the controller 42 no longer receives the moisture signal. The looping notification mode helps to remind the guardians to attend to the clothing article 6 to prevent rashes and other skin diseases on a wearer.

The residual power detector 27 detects the residual power of the battery 26. When the residual power detected by the residual power detector 27 corresponds to a low residual power level, the processor 24 configures the wireless transmitter 25 to transmit a low battery signal. When the controller 42 receives the low battery signal for a first time via the wireless receiver 41, the controller 42 executes the normal notification mode to configure the notification module 43 to output the low battery notification signal, and at the same time configures the timer 44 to start counting.

The controller 42 configures the notification module 43 to stop outputting the low battery notification signal when the timer 44 has counted to the predetermined period value. The low battery notification signal is at least one of the light emitted by the light emitting component 431 and the sound outputted by the speaker 432. Similarly, after the notification module 43 stops outputting the low battery notification signal when the timer 44 has counted to the predetermined period value, if the controller 42 continues to receive the low battery signal via the wireless receiver 41 (such as when the battery 26 is yet to be replaced), the controller 42 executes the looping notification mode to configure the notification module 43 to output the low battery notification signal intermittently until the controller 42 no longer receives the low battery signal. In the same manner, when the power in the power source 45 is low, the controller 42 configures the notification module 43 to output the low power notification signal until the power in the power source 45 is no longer low. The low battery notification signal and the lower power notification signal prevent a situation where the guardian fails to attend to the clothing article 6 due to insufficient power in the battery 26 or the power source 45.

In this embodiment, the moisture detector 22 and the first portion 31 of the clip unit 3 are removable from the sleeve body 21. The casing 23 that contains the processor 24, the wireless transmitter 25, the battery 26 and the residual power detector 27 is removable from the clip unit 3. The transmission wire 28 is also removable from the casing 23. Such removable design provides convenience in washing, repair and replacement of individual units in the wetness notification system.

Figure 5:
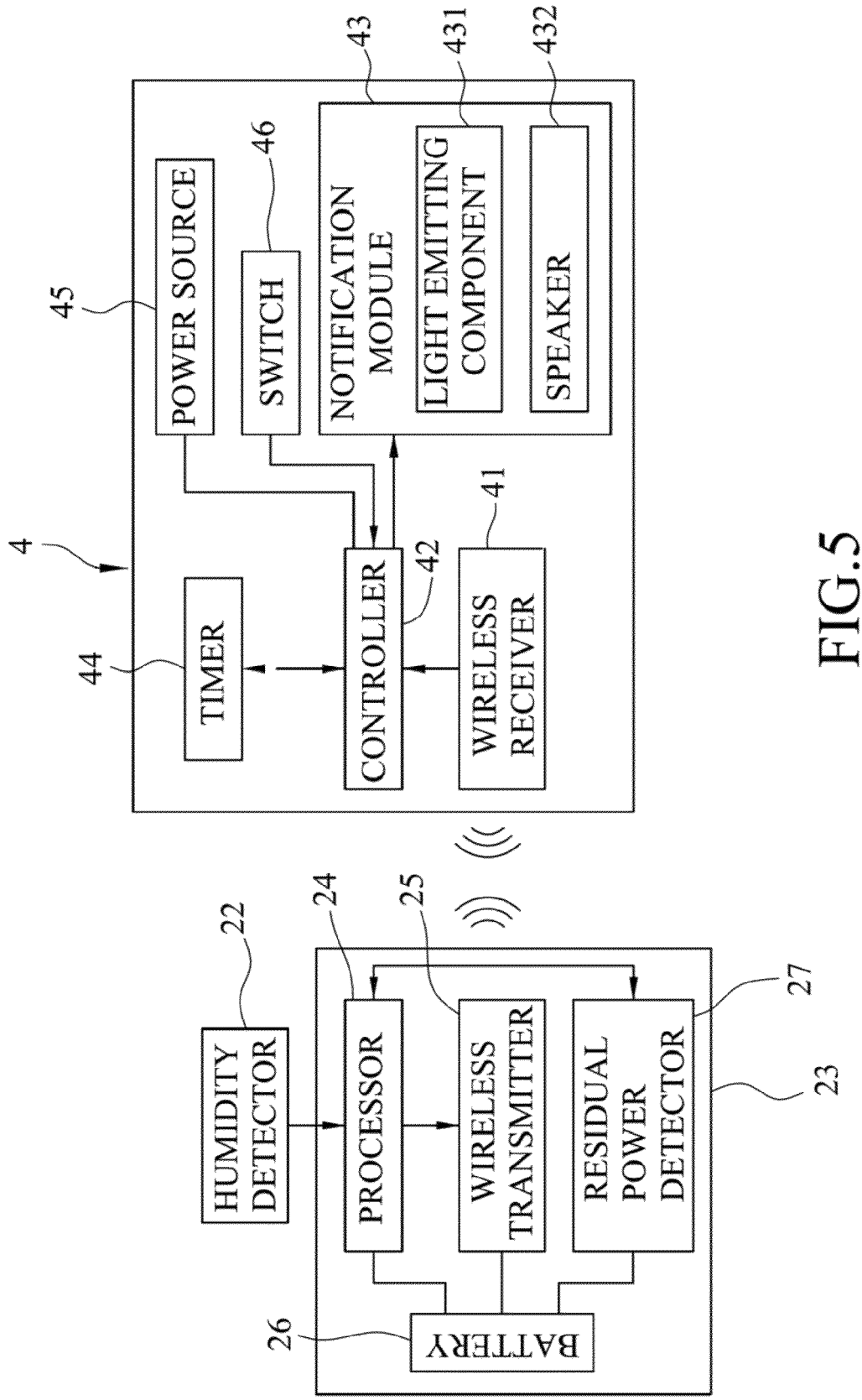
FIG. 5 is a schematic block diagram illustrating a second preferred embodiment of the present invention.

Referring to FIG. 5, the second preferred embodiment of the present invention differs from the first preferred embodiment, in that the second preferred embodiment further includes a switch 46 electrically coupled with the controller 42. When the controller 42 executes the normal notification mode to configure the notification module 43 to output one of the wetness notification signal and the low battery notification signal, the controller 42 configures the timer 44 to start counting, and the switch 46 may be operated by the guardian to control the controller 42 to control in turn the notification module 43 to stop outputting one of the wetness notification signal and the low battery notification signal. When the timer 44 has counted to the predetermined period value and the controller 42 continues to receives the one of the moisture signal and the low battery signal via the wireless receiver 41, the controller 42 executes the looped notification mode to configure the notification module 43 to output the corresponding one of the wetness notification signal and the low battery notification signal intermittently.

The wetness notification system of the present invention has a simple and detachable structure that lowers manufacturing costs. The clip unit 3 can be removably clipped to different suitable locations of the clothing article 6 for wetness detection, and therefore the detection unit 2, the clip unit 3 and the positioning member 5 of the wetness notification system can be reused again after they have been removed. In addition to wetness detection by the moisture detector 22 and the processor 24, the residual power detector 27 detects the residual power of the battery 26, and the notification module 43 outputs a notification signal (such as light and/or sound) for more than once when wetness or low residual power is detected, such that the guardian can attend to the clothing article 6 or replace the battery 26. Also, when insufficient power in the power source 45 is detected, the controller 42 drives the notification module 43 to output a low power notification signal. In such manner, the guardian can attend to the clothing article 6 to prevent rashes and other skin diseases on a wearer and be notified to replenish the power in the wetness notification system. Moreover, the wetness notification system includes the moisture detector 22 and the first portion 31 of the clip unit 3 that are removable from the sleeve body 21, the casing 23 that is removable from the clip unit 3, and the transmission wire 28 that is removable from the casing 23, and such removal design provides convenience in washing, repair and replacement of individual units in the wetness notification system.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A wetness notification system for detecting wetness in a clothing article that is configured for absorbing urine, the wetness notification system comprising:
    a detection unit including a sleeve body, a moisture detector that is connected to an outer side surface of the sleeve body and that outputs a moisture signal corresponding to a surrounding moisture detected thereby, a casing, a processor that is disposed in the casing and that is electrically connected with the moisture detector, a wireless transmitter that is disposed in the casing and that is electrically connected with the processor, and a battery that is disposed in the casing and that provides electric power to the moisture detector, the processor and the wireless transmitter, wherein the processor receives the moisture signal outputted by the moisture detector, and configures the wireless transmitter to transmit the moisture signal when the moisture signal corresponds to a moist condition of the surrounding moisture detected by the moisture detector;
    a clip unit including a first portion removably inserted into the sleeve body, a curved second portion that extends from the first portion, and a third portion that extends from the curved second portion, the casing being removably disposed on the third portion of the clip unit, the third portion cooperating with the first portion to clip the detection unit onto the clothing article in a manner that the sleeve body and the moisture detector are disposed at an inner side of the clothing article and that the third portion is disposed at an outer side of the clothing article; and
    a receiver unit including a wireless receiver to communicate wirelessly with the wireless transmitter, a controller electrically connected with the wireless receiver, and a notification module electrically connected with the controller; wherein when the controller receives the moisture signal via the wireless receiver, the controller drives the notification module to output a wetness notification signal.

2. The wetness notification system as claimed in claim 1, wherein the clip unit is a hollow frame made from a bent resilient loop-shaped member, and the third portion has a width that is smaller than that of the first portion.

3. The wetness notification system as claimed in claim 1, wherein the detection unit further includes a transmission wire, one end of the transmission wire being electrically connected with the moisture detector, another end of the transmission wire including a plug that is plugged into the casing 23 to electrically connect the moisture detector with the processor.

4. The wetness notification system as claimed in claim 3, further comprising a positioning member that is provided on the clip unit and that positions the transmission wire on the clip unit.

5. The wetness notification system as claimed in claim 4, wherein the positioning member includes a slit for receiving a section of the transmission wire.

6. The wetness notification system as claimed in claim 1, wherein:
    the detection unit further includes a residual power detector disposed in the casing and electrically connected with the battery and the processor, the residual power detector detecting a residual power of the battery, the processor configuring the wireless transmitter to transmit a low battery signal when the residual power detected by the residual power detector corresponds to a low residual power level; and
    when the controller receives the low battery signal via the wireless receiver, the controller configures the notification module to output a low battery notification signal.

7. The wetness notification system as claimed in claim 6, wherein:
    the controller is operable in one of a normal notification mode and a looping notification mode;
    when the controller receives one of the moisture signal and the low battery signal for a first time via the wireless receiver, the controller executes the normal notification mode to configure the notification module to output a corresponding one of the wetness notification signal and the low battery notification signal for a predetermined time period; and
    at the end of the predetermined time period, when the controller continues to receives said one of the moisture signal and the low battery signal via the wireless receiver, the controller executes the looping notification mode to configure the notification module 43 to output the corresponding one of the wetness notification signal and the low battery notification signal intermittently.

8. The wetness notification system as claimed in claim 7, wherein:
the receiver unit further includes a timer electrically coupled with the controller; and
when the controller executes the normal notification mode,
the controller configures the timer to start counting when the controller configures the notification module to output one of the wetness notification signal and the low battery notification signal, and
the controller configures the notification module to stop outputting said one of the wetness notification signal and the low battery notification signal when the timer has counted to a predetermined period value.

9. The wetness notification system as claimed in claim 7, wherein:
the receiver unit further includes a timer electrically coupled with the controller and a switch 46 electrically coupled with the controller;
when the controller executes the normal notification mode, the controller configures the timer to start counting, and the switch is operable to control the controller to control in turn the notification module to stop outputting one of the wetness notification signal and the low battery notification signal, and
the controller executes the looped notification mode when the timer has counted to a predetermined period value and the controller continues to receives said one of the moisture signal and the low battery signal via the wireless receiver.

10. The wetness notification system as claimed in claim 6, wherein:
the notification module includes at least one of a light emitting component for emitting light and a speaker for outputting sound; and
each of the wetness notification signal and the low battery notification signal is at least one of the light emitted by the light emitting component and the sound outputted by the speaker.

11. The wetness notification system as claimed in claim 6, wherein the receiver unit further includes a power source electrically coupled with the controller to provide electric power for the receiver unit, and the controller configures the notification module to output a low power notification signal when power of the power source is insufficient.

\* \* \* \* \*